(12) United States Patent
Rosen et al.

(10) Patent No.: US 11,623,015 B2
(45) Date of Patent: Apr. 11, 2023

(54) SYSTEM AND METHOD FOR SAFELY IRRADICATING PATHOGENS

(71) Applicant: FREESTYLE PARTNERS LLC, Detroit, MI (US)

(72) Inventors: Jennifer K Rosen, Detroit, MI (US); Benjamin X Feeney, Nashville, TN (US); Gregory D DeGrazia, Birmingham, MI (US)

(73) Assignee: FREESTYLE PARTNERS LLC, Detroit, MI (US)

( * ) Notice: Subject to any disclaimer, the term of this patent is extended or adjusted under 35 U.S.C. 154(b) by 0 days.

(21) Appl. No.: 17/955,168

(22) Filed: Sep. 28, 2022

(65) Prior Publication Data

US 2023/0039126 A1 Feb. 9, 2023

Related U.S. Application Data

(63) Continuation of application No. PCT/US2021/025411, filed on Apr. 1, 2021.
(Continued)

(51) Int. Cl.
*A61L 2/10* (2006.01)
*A61L 2/08* (2006.01)
(Continued)

(52) U.S. Cl.
CPC ............... *A61L 2/10* (2013.01); *A61L 2/084* (2013.01); *A61L 2/24* (2013.01); *A61L 2/26* (2013.01);
(Continued)

(58) Field of Classification Search
CPC ... A61L 2/10; A61L 2/084; A61L 2/24; A61L 2/26; A61L 2202/11; A61L 2202/14
See application file for complete search history.

(56) References Cited

U.S. PATENT DOCUMENTS

| 2003/0113230 A1 | 6/2003 | Cordery et al. |
| 2007/0053188 A1 | 3/2007 | New et al. |

(Continued)

OTHER PUBLICATIONS

PCT/US2021/025411 International Search Report and Written Opinion dated Apr. 1, 2021.

*Primary Examiner* — Nicole M Ippolito
*Assistant Examiner* — Hanway Chang
(74) *Attorney, Agent, or Firm* — Gregory D. Degrazia; Miller, Canfield Paddock & Stone (57) ABSTRACT

A system for eradicating pathogens is disclosed. A lamp is provided that emits a far-ultraviolet C (far-UVC) light generates an irradiation zone. A biometric sensor determines whether an individual is present in the irradiation zone. The biometric sensor signals a processor to determine whether the individual has been exposed to a threshold limit of far-UVC light. The processor determines whether the time an individual has been in the irradiation zone exceeds a threshold limit. If the individual has been in the irradiation zone a period of time exceeds the threshold, the lamp is deactivated. A pathogen detection sensor provides user feedback of the existence pathogens and signals the processor to terminate irradiation or provide user feedback to terminate irradiation. The system and method are included in a passenger compartment of a vehicle to eradicate pathogens on surfaces and aerosol. Threshold limits allow eradication while the vehicle is occupied.

11 Claims, 7 Drawing Sheets

Related U.S. Application Data

(60) Provisional application No. 63/003,560, filed on Apr. 1, 2020.

(51) Int. Cl.
*A61L 2/26* (2006.01)
*A61L 2/24* (2006.01)

(52) U.S. Cl.
CPC ........ *A61L 2202/11* (2013.01); *A61L 2202/14* (2013.01)

(56) References Cited

U.S. PATENT DOCUMENTS

| | | |
|---|---|---|
| 2008/0103560 A1 | 5/2008 | Powell et al. |
| 2017/0069192 A1 | 3/2017 | Sood et al. |
| 2017/0216472 A1 | 8/2017 | Stibich et al. |

SYSTEM AND METHOD FOR SAFELY IRRADICATING PATHOGENS

CROSS REFERENCE TO RELATED APPLICATIONS

PRIOR APPLICATIONS

The present application claims priority as a bypass continuation application of Patent Application No. PCT/US2021/025411 filed on Apr. 1, 2021, which claims priority to U.S. Provisional Patent Application No. 63/003,560, filed Apr. 1, 2020, both of which are incorporated herein by reference in their entirety.

TECHNICAL FIELD

The present application relates generally toward a system and method for safely eradicating pathogens from a target area. More specifically, the present application is directed toward a device, system and method that uses far-ultraviolet C (far-UVC) light for eradicating pathogens and is capable of monitoring the target area and controlling and amount of exposure to far-UVC light in the target area for eradicating pathogens.

BACKGROUND

With the rapid expansion of biological pathogens, it has become increasingly important to find novel ways to eradicate pathogens in a manner that is safe for human exposure. Increasingly, chemicals have been implemented to disinfect surfaces in public places. However, the increased use in chemicals is presenting health hazards that are only beginning to manifest. In response to an increased need to eradicate biological pathogens, various forms of ultraviolet light have been developed to disinfect aerosol pathogens and surface pathogens.

The use of ultraviolet light has proven particularly effective for eradicating pathogens when ultraviolet-C(UVC) light is incorporated into an illumination device. UVC light emissions range between about 100 nm and 280 nm. While UVC light has proven quite effective in eradicating pathogens, it is known to exhibit unsafe attributes when exposed to human epidermis and eye tissue. Conventional UVC light has been proven to cause skin cancer and cataracts. Therefore, the use of UVC light is limited in scope to situations where no human exposure is permitted, and substantial precautions are required to prevent any human exposure. A subset of UVC light, commonly referred to as far-UVC light, has recently gained some notoriety due to its ability for safely eradicating pathogens while potentially being safe for limited human exposure. When filtered, far-UVC light transmits UV light between about 200 to 230 nm. When unfiltered, UV light transmits above 230 nm a level at which it is believed adversely affects human epidermis by causing DNA damage. Whether filtered or not, far-UVC light presents peak irradiation at 222 nm.

While far-UVC light has shown promise for eradication of pathogens, its proposed uses have been for ceiling mounted systems within buildings for eradicating aerosol pathogens providing slow eradication on distant surfaces taking upwards of thirty minutes. This slow eradication on surfaces using ceiling mounted devices is problematic fix high traffic or high use areas that cannot be made vacant for thirty or more minutes while waiting for a surface to be disinfected. When locating a lamp that generates far-UVC light in close proximity to a surface being disinfected, pathogens may be eradicated more rapidly, human exposure limits may be significantly reduced. Therefore, there exists a need for a device capable of rapidly eradicating pathogens, while optimizing far-UVC irradiation time and limiting exposure to regulatory thresholds.

SUMMARY

A method and system for eradicating pathogens is disclosed. A lamp is provided that emits a far-ultraviolet C (far-UVC) light generates an irradiation zone. A biometric sensor determines whether an individual is present in the irradiation zone. The biometric sensor signals a processor to determine whether the individual has been exposed to a threshold limit of far-UVC light. The processor determines whether individual has been in the irradiation zone exceeds a threshold limit. If the individual has been in the irradiation zone a period of time that meets or exceeds the threshold, the lamp is deactivated. The system includes a pathogen detection sensor that provides user feedback of the existence or non-existence of pathogens and signals the processor to activate irradiation when presence of pathogens are detected or terminate irradiation or provide user feedback to terminate irradiation when no pathogens are detected. The system and method are included in a passenger compartment of a vehicle to eradicate pathogens on surfaces and aerosol. Threshold limits are included to allow eradication while the vehicle is occupied.

The problems identified in the prior art are associated with close proximity eradication of pathogens using UVC light or far-UVC when individuals are present either as a user or by way passive presence. While far-UVC light, and more specifically filtered far-UVC light have good indications of safe irradiation of human epidermis and even eyes, rigid safety standards remain in place prevented more than limited exposure by humans. The invention of the present application solves these problems by providing a system to limit human exposure, and even include these pathogen eradication systems in small compartments, such as passenger vehicles allowing more integrated use far-UVC light than prior art systems.

BRIEF DESCRIPTION OF THE DRAWINGS

Other advantages of the present invention will be readily appreciated as the same becomes better understood by reference to the following detailed description, when considered in connection with the accompanying drawing, wherein.

DETAILED DESCRIPTION

Figure 1A:
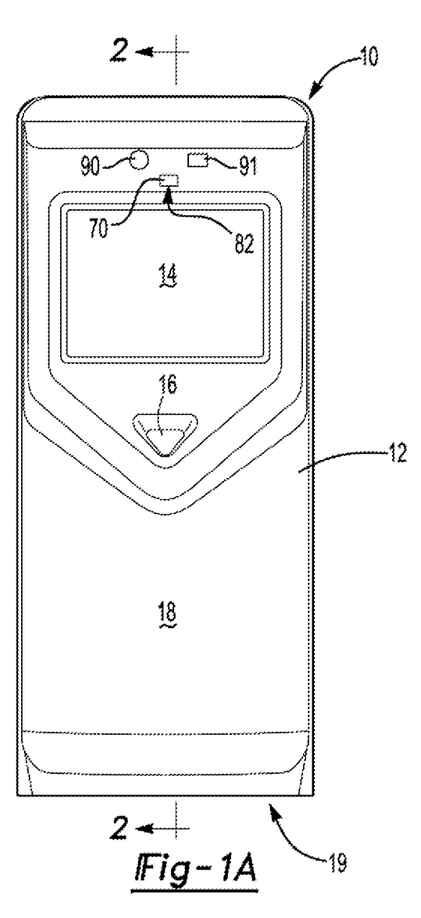
FIG. 1A shows a face side view of one embodiment of a device of the present invention.

Referring to FIG. 1A, a handheld light assembly of the present invention is generally shown at 10. The assembly 10 includes a housing 12 that defines a lamp opening 14 as will be explained further herein below. A secondary light opening 16 is defined by the housing 12 approximate the lamp opening 14. Both openings 14,16 are defined by a face side 18 of the housing 12. The purpose of the lamp opening 14 in the secondary light opening 16 will be explained further herein below.

Devices of this type are contemplated in U.S. patent application Ser. No. 17/119,440 filed Dec. 11, 2020, HANDHELD FAR-UVC DEVICE WITH LIDAR MEASUREMENT AND CLOSED LOOP FEEDBACK; Ser. No. 16/811,522 filed Mar. 6, 2020 PORTABLE AND DISPOSABLE FAR-UVC DEVICE; Ser. No. 16/809,976 filed Mar. 5, 2020; PORTABLE AND DISPOSABLE FAR-UVC DEVICE; 62/963,682 filed Jan. 21, 20202 PORTABLE AND DISPOSABLE UV DEVICE; Ser. No. 16/279,253 filed Feb. 19, 2019 PORTABLE AND DISPOSABLE FAR-UVC DEVICE; 62/694,482 filed Jul. 6, 2018 PORTABLE AND DISPOSABLE FAR-UVC DEVICE; and 62/632,716 filed Feb. 20, 2018 PORTABLE AND DISPOSABLE FAR-UVC DEVICE, the contents of each of which are incorporated herein by reference.

Figure 1B:
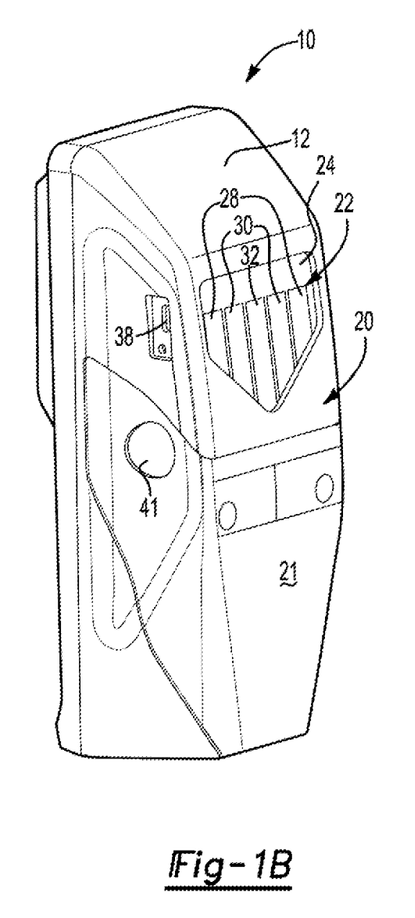
FIG. 1B shows a backside perspective view of the device of FIG. 1A.

The housing 12, as best shown in FIG. 1B includes a backside 20 that defines an indicator opening 22. A removable grip 21 receives the backside 20 of the housing 12 and is removably retained by the complementary abutting surfaces 23, 25 (FIG. 3) respectively that each defines a convex shape providing an interference retention system. The removable grip 21 is cleanable by way of illumination with the assembly 10 as will become more evident herein below or is cleanable by alternative methods in a desired manner. When mated, the face side 18 and the backside 20 define a stand 19 so that the assembly 10 may stand upright, when desired, orienting the lamp 14 in a vertical direction.

An indicator 24 encloses the indicator opening 22. The indicator 24 signals an operator whether a distance between a lamp 26 (FIG. 4) and a surface being irradiated is within a predetermined distance to a pathogen to provide optimal eradication energy. For example, a first telltale 28 signals the operator if the distance is beyond a predetermined distance (or in some instances not spaced enough). In one embodiment, the telltale illuminates red or other color signaling the operator if the lamp is too far, or too close. The indicator 24 generate a second signal by way of 2nd telltale 30 indicating when the lamp is proximate the predetermined distance to the surface being irradiated. In one embodiment, the second telltale illuminates in yellow to signal the lamp 26 is proximate the predetermined distance to the surface 60 (FIG. 4) being irradiated. When the lamp 26 is disposed at the predetermined distance to the surface being irradiated, a third telltale 32 illuminates in green to signal the operator the lamp is operating at optimal efficiency at the predetermined distance. Each telltale 28, 30, 32 is illuminated by a corresponding light 29, 31, 33 (FIG. 3) respectively, in this embodiment a corresponding light emitting diode.

It should be understood to those of ordinary skill in the art the different telltales or indicators may be used to signal an operator whether the assembly 10 is being used properly by way of distance from a surface being disinfected. These include, but are not limited to, blinking lights, sound or audible feedback cues, vibration or any indicator that would suffice to signal an operator the lamp 26 is disposed at the proper distance from a surface being irradiated for providing optimal eradication of pathogens. As described in further detail hereinbelow, these signals can be used to provide additional information to a user including, but not limited to indications of exposure limits; indication of existence or eradication of pathogens and the like.

While "surface" is used throughout the application, it should be understood that the invention of the present application provides for rapid eradication of pathogens not only on inanimate object, but also on epidermis including hands, legs arms, and even a face of an individual. As will be explained further herein below, disinfecting skin at a rapid pace is now possible without requiring the use of soap or chemicals. In a matter of seconds an individual's hands my disinfected with the handheld assembly 10 of the present invention. Furthermore, abrasions and wounds may also be rapidly disinfected in a safe and immediate manner while awaiting administered antibiotics to begin working. Even though illumination energy is quite high when the lamp 26 is disposed at close ranges to epidermis, such as, for example, one inch, the filtered far-UVC light will not penetrate the epidermis while rapidly eradicating a wide range of pathogens in seconds.

Figure 2:
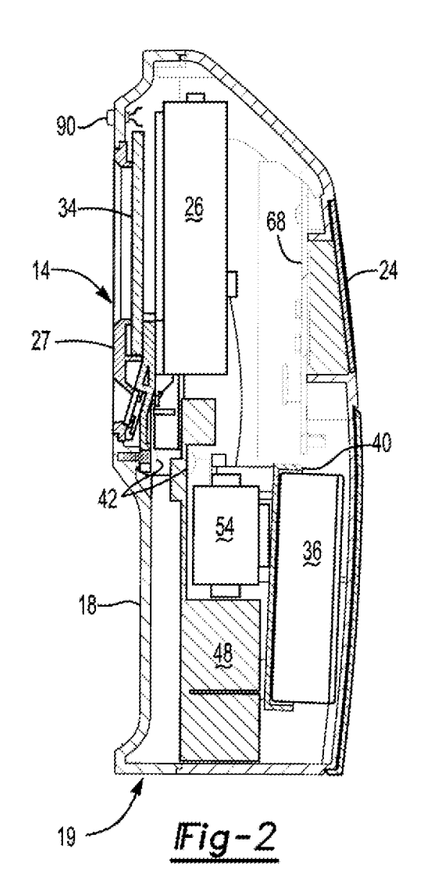
FIG. 2 shows a cross-sectional view of the device of FIG. 1A along a centerline.
Figure 3:
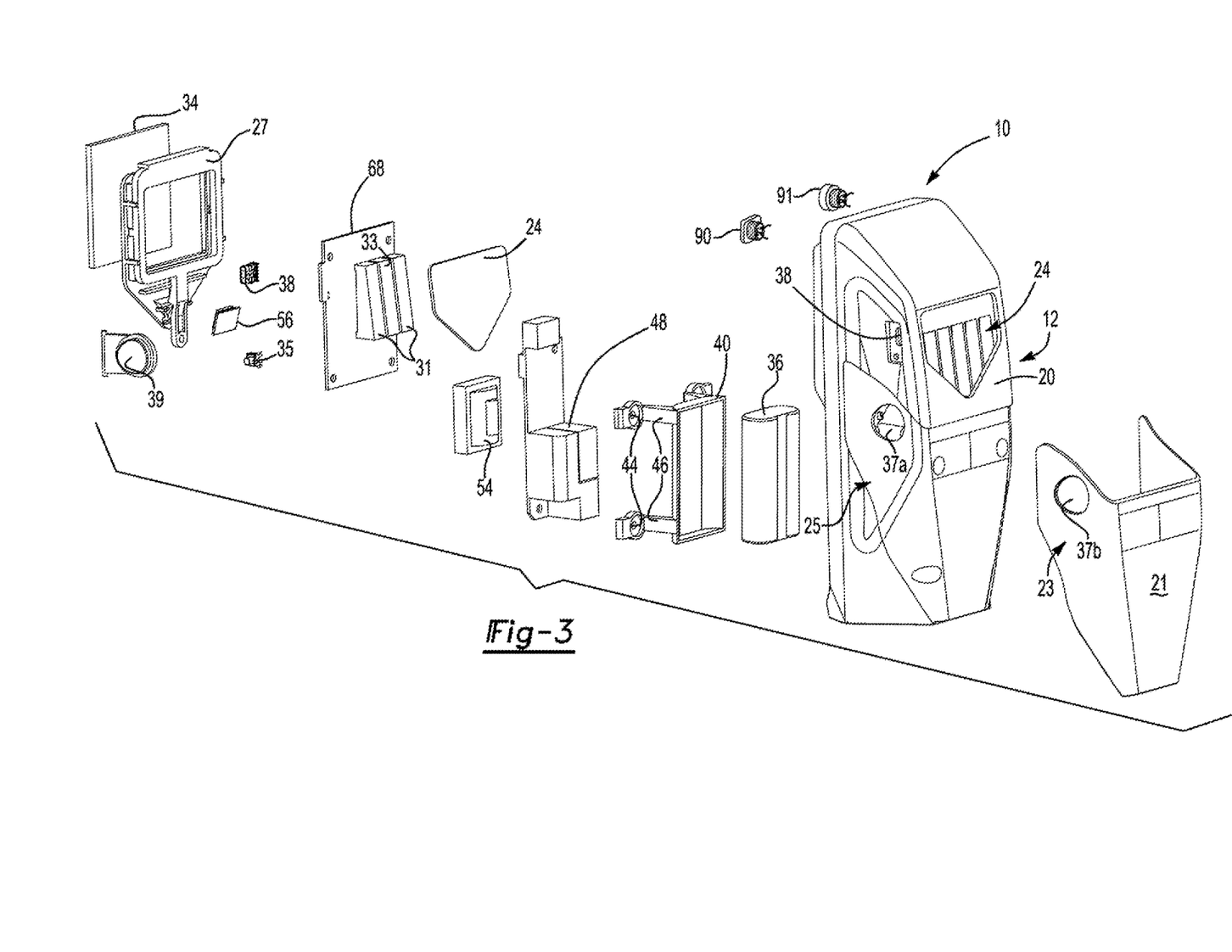
FIG. 3 shows an exploded view of the device of FIG. 1A.

Referring now to FIG. 3, the lamp 26 (FIG. 2) is activated by depressing switch 35 that partially extends through opening 37a defined by the backside 20 of the housing 12 and an opening 37b defined the removable grip 21, each of which are aligned when the removable grip 21 is disposed in place on the housing 12. A switch cover 39 is disposed between the switch 35 and the backside 20 of the housing and conceals the switch 35 so that when depressed, an operator does not contact the switch 35 but contacts the switch cover 39. A still further embodiment includes a protective barrier 41 (FIG. 1B) being affixed, either permanently or temporarily to the removal grip 21 over the grip opening 37b to prevent the switch cover 39 from becoming contaminated. In this manner the barrier 41 may also be disinfected with the grip 21 when removed from the housing 12. In one embodiment, when the assembly 10 is supported in a vertical direction by the stand 19, the switch 35 optionally activates the processor 68 to power the lamp 26 for a predetermined amount of time allowing a user to disinfect, for example his or her hands, the removable grip 21, or any other object without continuously depressing the switch 35, or even having to hold the device 10. Because the illumination wavelength of the lamp 26 is filtered restricting transmission wavelength to below 230 nm, and not harmful to eyes and epidermis, the lamp 26 may be illumined while disposed in a vertical orientation while not requiring the use of safety equipment. Alternatively, because activating or deactivating the device 10 may contaminate the device 10 via human touch, optionally, the device 10 may also or otherwise be activated/deactivated through facial/eye recognition (as seen in some mobile devices) and/or through voice activation (similar to voice assistants on mobile devices). The device 10 may also or otherwise be activated/deactivated through specific movements (i.e., shaking it, moving it in a specific motion, etc.).

Referring now to FIG. 2, a cross sectional view through line 2-2 of FIG. 1A is shown. The lamp 26 is disposed over the lamp opening 14 in a fixed location by lamp frame 27 for generating illumination through the lamp opening 14 onto a target surface 60. The lamp 26 is adapted to use a variety of illumination techniques including krypton chloride tubes, light emitting diodes, or any other illumination system capable of transmitting light at a peak wavelength 222 nm. In one embodiment, the lamp 26 is filtered to eliminate light having a wavelength above about 230 nm. Therefore, disinfecting light is transmitted at a wavelength between about 200 nm and 230 nm. In one embodiment, fused silica protective cover 34, or equivalent is placed over the lamp opening 14 to protect the lamp during use. Fused silica protective cover 34 is believed durable enough to withstand the energy generated by far-UVC light emissions without significant degradation while allowing light transmission without significantly reducing irradiation power of the lamp 26. However, other cover compositions are within the scope of this invention, including, but not limited to quartz or any other material capable of allowing transmission of far-UVC light without becoming substantially degraded. It should also be understood that lens and cover are used interchangeably throughout this specification but that each refers to the element 36 disposed between the lamp 26 or tubes contained in the lamp and the surface 60 being irradiated so that the far-UVC light is transmitted through the lens 36. Still further, the filter (not shown) that filters the far-UVC light to eliminate or substantially reduce wavelengths above 230 nm may be part of the lens 36. It should be understood that alternative far-UVC light is within the scope of this invention including light emitting diodes or alternative sources that do not transmit light above about 230 nm but provide peak irradiation at or about 222 nm capable of eradicating pathogens while being substantially safe for humans.

Figure 7:
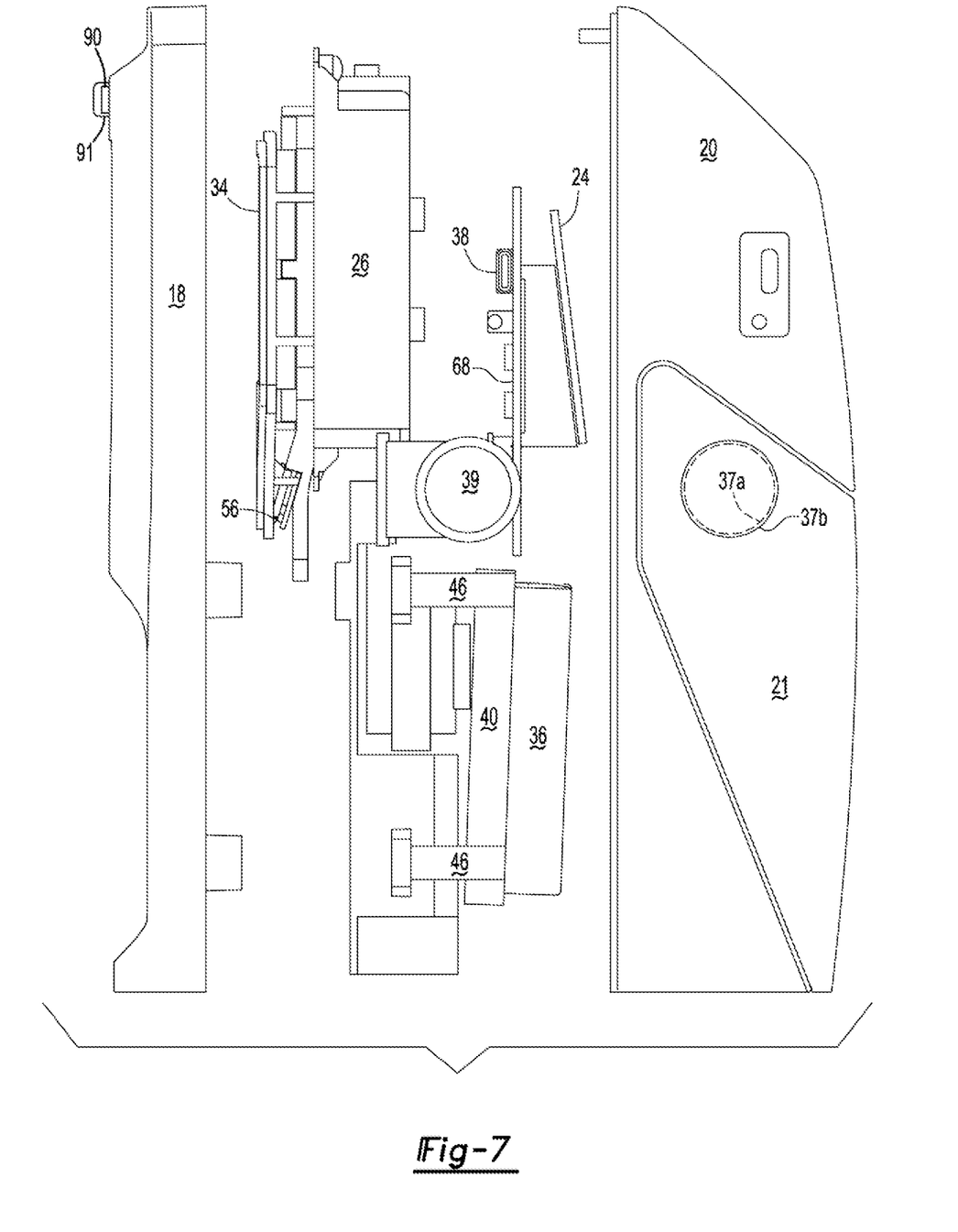
FIG. 7 shows an expanded view of the device of FIG. 1A with the housing separated.

The lamp 26 is powered via power pack 36. The power pack 36 is rechargeable through plug-in charging port 38. In one embodiment, the power pack 36 includes two lithium ion 18650 PMI cells (not shown) providing about 3.6 volts each. Therefore, the power pack 36, when charged, provides about 7.2 volts. Alternatively, the lamp 26 is powered by electrical current provided through the charging port 36. The power pack 38 is received by a power pack support 40 that secures the power pack 36 to screw bosses located on an inner surface of the face side 18 of the housing 12 via fasteners (not shown) in a known manner. The fasteners are received through support apertures 44 defined by support legs 46 (FIG. 7).

The support legs 46 allow the power pack support 40 to straddle an inverter 48 that is also secured to the face side 18 of the housing 12. The inverter 48 receives current from the power pack 36 at 7.2 volts and shapes the current wavelength in a known manner so it that may be received by the lamp 26. The inverter 48 is disposed upon an inverter frame 50 that is secured to the face side 18 of the housing 12 by fasteners received through inverter frame apertures 52.

A transformer 54 steps up the voltage from about 7.2 volts generated by the power pack 36 to about 4,000 volts to provide sufficient energy to power the lamp 26. In one embodiment, the inverter 48 is a Stratheo inverter. However, it should be understood that any inverter/transformer combination capable of shaping the current wavelength and stepping up voltage to about 4,000 volts will suffice. The transformer 54 is also mounted on the inverter frame 50 to reduce overall size of the inverter 48 transformer 54 combination.

Figure 4:
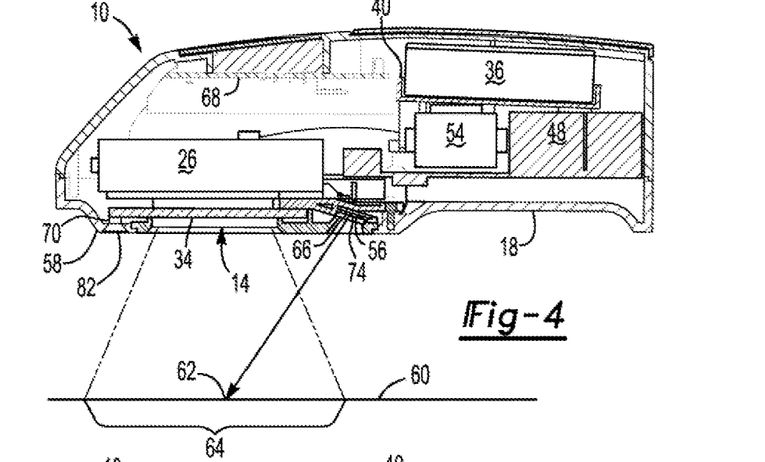
FIG. 4 shows a cross-sectional view of the device of FIG. 1A having the distance measuring device activated.
Figure 5:
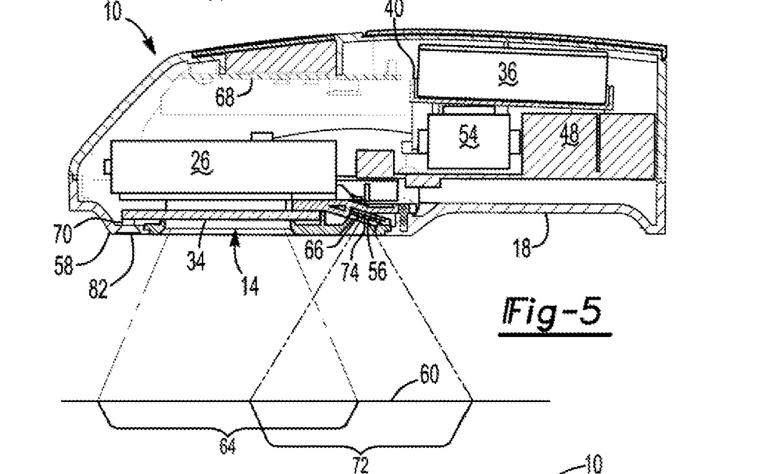
FIG. 5 shows a cross-sectional view of the device of FIG. 1A having an alternative distance measuring device activated.

Referring now to FIGS. 4 and 5, a distance measuring device 56 is secured to a lamp frame 58 that also secures the lamp 26 to the face side 18 of the of the housing 12. The lamp frame 58 is oriented so that the lamp 26 is disposed horizontally to a surface 60 being disinfected when the assembly 10 is in use as is best shown in FIG. 4. The distance measuring device 56 is offset from the lamp 26 and disposed at an angle relative to the lamp 26. In one embodiment, the distance measuring device 56 transmits a signal to a center portion 62 of an irradiation zone 64 on the surface 60 defined by the lamp 26. The distance measuring device 56 includes a sensor 66 that receives reflected feedback of the signal from the center portion 62. The sensor 66 provides the feedback data to the processor 68 to calculate a vertical distance from the lamp 26 to the center portion 62 of the irradiation zone 64. Therefore, even though the distance measuring device 56 is offset from the lamp 26, it measures a precise vertical distance between the lamp 26 and the surface 60 being irradiated at the location of the highest energy level, the purpose of which will become more evident as explained below.

In one embodiment, the distance measuring device 56 is a lidar system transmitting a laser beam 63 to the center portion 62 of the irradiation zone 64. The laser beam 63 is either visible or invisible. When visible, the laser beam provides user feedback to the center portion 62 of the irradiation zone 64. In another embodiment, the distance measuring device 56 takes the form of an infrared light that transmits to the center portion 62 of the irradiation zone 64 and the sensor 66 is an infrared sensor that detects reflected light from the center portion 62 for signaling the processor to calculate vertical distance from the center portion 62 to the lamp 14. Other types of distance measuring devices are within the scope of this invention including radar, photogrammetry and the like so long as the center portion 62 of the irradiation zone 64 can be detected. It should also be understood that a time of flight determination between the light (or other signal) and sensor 66 detecting reflection has provided sufficient accuracy for the processor 68 to calculate vertical distance between the central portion 62, or point as the case may be, and the lamp 26.

As set forth above, the processor 68 signals the indicator 24 to signal if the lamp 26 is located at a predetermined distance from the center portion 62 of the irradiation zone. In one embodiment, the indicator 24 signals proper distance is maintained for rapid eradication of pathogens when the lamp 26 is disposed within a range of distances, such as, for example between one and two inches. Therefore, the user is provided feedback that the lamp 26 is maintained within in a proper range even when three dimensional surfaces are being irradiated for eradicating pathogens. It has been determined that distance is inversely proportional to the rate of energy that reaches the surface 60. The less the distance the lamp 14 is to the surface 60 being irradiated, the higher the rate of ultraviolet energy transfer to the surface 60 is achieved for rapid eradication of surface pathogens.

The lamp 14 was tested at a range of distances to ascertain the amount of energy required to eradicate pathogens, both with the fused silica protective lens 34 and without the fused silica protective lens 34. The results showed only a small decrease in the amount of far-UVC light energy when the fused silica lens 34 was employed. The results were measured in $\mu$Watts as is shown in Table 1.

TABLE 1

| Distance from Sensor | No Protective Cover | UV Fused Silica |
|---|---|---|
| 1" (2.5 cm) | 3202 | 3030 |
| 2" (5.08 cm) | 1770 | 1650 |
| 4" (10.16 cm) | 685 | 634 |
| 6" (15.24 cm) | 353 | 330 |

At a distance of about one inch from the surface 60 being irradiated, the lamp 14 provides 3030 µW rate of energy transfer. Alternatively, a distance of about six inches from the surface 60 being irradiated, the lamp 14 provides 330 µW of ultraviolet energy transfer. The amount of energy transfer translates into the amount of time necessary to eradicate certain pathogens. The fused silica protective cover (or lens) 34 reduces to some extent the amount of irradiation energy at the surface 60 being irradiated. Surprisingly, the amount of reduction of irradiation by the fused silica lens 34 energy at the surface 60 decreases as distance increases. Therefore, the reduction of irradiation energy attributed to the protective fused silica lens 34 is inversely proportional to the distance between the lamp 26 and the surface.

Furthermore, the irradiation energy when the lamp 14 is spaced a distance of about one inch from the surface being irradiated is between about 1.8 and 1.83 (about a factor of 2) times greater than when the distance between the lamp 14 and the surface 60 being irradiated is about two inches from the lamp 14. The lamp 14 provides between about 4.67 and 4.77 (about a factor of five) times more surface energy when disposed about one inch from the surface 60 being irradiated than when the lamp 14 is disposed about four inches from the surface being irradiated. The lamp 14 provides between about 9.07 and 9.18 (about a factor of ten) times more surface energy when disposed at about one inch from the surface 60 being irradiate than when the lamp 14 is disposed at about six inches from the surface 60 being irradiated.

Test results show that Covid-19 is eradicated by providing a 3 Log reduction (99.9% eradication) in the pathogen in about one second when the lamp 14 is disposed at a distance of about one inch from the surface 60 being irradiated. Alternatively, Covid-19 can be eradicated to a 3 Log reduction in about 9.5 seconds when the lamp 14 is disposed at a distance of about six inches from the surface 60 being irradiated. It should be understood by those of ordinary skill in the art that different pathogens require different doses of irradiation for full or 3 Log reduction on any surface. While a virus may require only one second of irradiation when the lamp 14 is disposed at one inch from the surface 60 being irradiated, a bacteria or spore may require several seconds of irradiation at the same distance. Furthermore, a 2 Log reduction providing 99% eradication of Covid-19 is achieved in about 0.1 seconds when the lamp 26 is spaced about one inch from the surface 60 being irradiated. Likewise, Covid-19 can be eradicated to a 2 Log reduction in about 0.95 seconds when the lamp 14 is disposed at a distance of about six inches from the surface 60 being irradiated. It should be apparent that determining an accurate distance of the lamp 26 from the surface 60 being irradiated is requisite when determining the level of a pathogen eradication being achieved.

FIG. 5 shows an alternative arrangement where the distance measuring device 56 transmits secondary light onto a measurement area 72 that intersects the irradiation zone 64 on the surface 64. In this embodiment, at least a portion of the measurement area 72 intersects the center portion 62 of the irradiation zone 64. The sensor 66 detects the reflected light, radar, or the like from the irradiation zone 64 for signaling the processor 68 to calculate a vertical distance between the lamp 26 and at least the center portion 62 of the irradiation zone 64.

It should also be understood that the distance measuring device 56 includes a transmitter 74 that transmits a signal to the surface 60 being irradiated by the lamp 26. The transmitter 74 is contemplated to project any of a non-visible laser beam, a visible laser beam, infrared light, radar, or the like enabling the sensor 66 to detect a reflected signal from the surface 60 being irradiate so that the processor 68 can calculate vertical distance between the lamp 26 and at least the center portion 62 of the irradiation zone 64.

Figure 6:
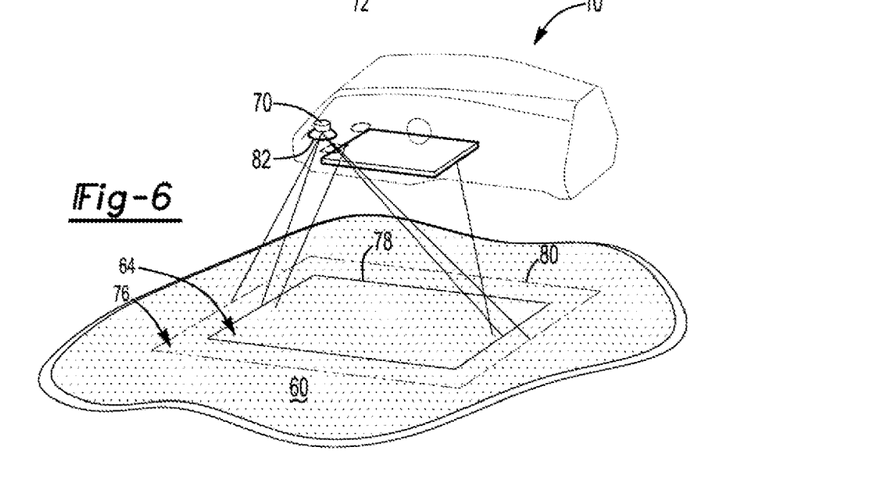
FIG. 6 shows partial perspective view of the device of FIG. 1A showing an identifier light source active for identifying irradiation zones.

Transmitted far-UVC light is largely in an invisible spectrum. Therefore, it is difficult for a user to fully identify a surface area in which the lamp 14 is achieving optimal irradiation. In addition, the lamp provides efficacy as the far-UVC light illumination on a surface extends radially outwardly from the central portion 62 (or area) of the irradiation zone 64. However, the energy transfer to the surface 60 diminishes beyond the irradiation zone 64 on the surface 60. While still providing efficacy, a secondary irradiation zone 76 located generally radially outwardly of the first irradiation zone 64 requires additional time in which to eradication pathogens. To assist the operator with identifying at least the irradiation zone 64, and also, when desired, a secondary irradiation zone 76, an identifier light source 70 projects a first ring 78 or equivalent around the primary irradiation zone 64 and second ring 80 or equivalent around the secondary irradiation zone 76 as is represented in FIG. 6. The identifier light source 70 is a separate light from the secondary light that is part of the distance measurement device 56.

The illumination by the identifier light source 70, in one embodiment, is modified by identifier light source lens 82 that focuses the light from the identifier light source 70 to focus the light so that the first ring 78 is disposed on the surface 60 immediately adjacent the broadest spatial boundary of the primary irradiation zone 64 and the second ring 80 is disposed immediately adjacent the broadest spatial boundary of the secondary irradiation zone 76. A diameter of the first ring 78 and the second ring 80 increase proportionally with the vertical distance between the lamp 26 and the center portion 62 of the irradiation zone an equal amount to the broadest spatial boundary of the primary irradiation zone 64 and the secondary irradiation zone 76. In this manner, the identifier light source lens 82 is configured in a correlated manner so that angular displacement of the refracted light generates rings 78, 80 that increase in diameter at a same rate as does the far-UVC light in each of the first irradiation zone 64 and the second irradiation zone 76. Furthermore, the rings 78, 80 are transmitted on three dimensional surfaces providing identification that an object on a flat surface is within the irradiation zones 64, 76. The combination of the rings 64, 76 and the distance measuring device 56 providing user feedback via the indicator 24 enables a user, for example, to ascertain the viability of pathogen eradication that is achieved when used on inanimate objects and even on hands or other parts of the human anatomy.

In a further embodiment, the device 10 may emit visible light in various formats and/or shapes. For example, the formats and/or shapes may include names (or any other words), initials, symbols and/or shapes (e.g., a bat signal, stars, a flag, etc.) and/or photos, depending on the particular application or selection made by the user. Optionally, the user may upload one or more images to the device 10 to use for the emitted visible light (whereby the uploaded image is backlit by the light source so that the image is projected onto the surface). Optionally, when the device 10 is at an appropriate height, the customized visible light or projected image or icon may be in focus so that the user knows where the device 10 is aiming and that the device 10 is at the proper effective height or distance to eradicate pathogens. In another example, the device 10 may emit visible light in the shape of an icon that the user targets or aims at the surface to be irradiated. When the device 10 has run as long as is necessary to be effective, the visible light may turn off and/or fade and/or the device 10 may communicate to the user that the visible light may be disabled and/or that the device 10 needs to be recharged and/or the entire far-UVC unit must be replaced (e.g., when lack of visible light indicates that the far-UVC device 10 is no longer eradicating pathogens).

In a still further embodiment, the device 10 may emit sound in lieu of or in addition to visible light. For example, whether for the visually impaired or just as an alternate means to target an area for a set period of time, the device 10 may use sound or sonic messaging to communicate an amount of time to the user. In this embodiment, the processor 68 also includes an audio transistor for providing sound output. The device 10 emits a sound indicating an appropriate distance from a surface to eradicate pathogens at a predetermined time, so as to inform the user that the device 10 is at the appropriate or optimal distance from the surface being irradiated. For example, in addition to or alternatively to emitting visible light, the device 10 may include a sound activated feature that activates when the user is at the right and/or wrong distance for eradicating pathogens. The processor via the sound transistor may also provide audible user feedback if the device 10 is moving too quickly over a surface 60 to provide adequate eradication of pathogens identifiable by way of accelerometer and/or surface distance measurement.

In a further embodiment, the device 10 emits sound that indicate when the device 10 is getting too close or too far away from a target surface (e.g., using ultrasonic sensors, lidar or other distance detection systems). Such sounds may be permanent and/or customizable (similar to ringtones on mobile phones). When the device 10 has run as long as is necessary to be effective (e.g., eradicate pathogens), the sound may turn off and/or fade and/or the device 10 may communicate to the user that the device 10 needs to be recharged and/or the entire far-UVC unit must be replaced (e.g., when the lack of sound indicates that the far-UVC device 10 is no longer eradicating pathogens because the lamp has exceeded use limits). Optionally, the sound may be customizable to the preference of the user (such as in a similar manner as a cell phone's ringtones and notification sounds are customizable).

In a still further embodiment, the device 10 emits a scent instead of or in addition to emitting visible light for stationary use. Whether for the visually or audibly impaired, the device 10 emits scents to denote when the device 10 is in use or when the device 10 needs to be replaced or recharged. Instead of visible light, or in combination with the visible light, the device 10 emits scents that emanate when the device 10 is activated by way of an attachable fragrance unit proving user feedback as to operational disposition of the device 10 as is disclosed throughout the present application.

In some instances, human exposure may be limited by regulations or standards that are based upon an UVC or far-UVC light energy for a predetermine time period such as over eight or twenty-four hours. As such, the device 10 of the present invention includes a biometric sensor 90 capable of determining presence of human epidermis. Referring again to FIGS. 1-3, the biometric sensor 90 is represented in schematics on the handheld light assembly 10 also includes a biometric sensor 90 for detecting and identify an individual that is present in the irradiation zone 64. For example, the biometric sensor 90 detects the presence of human epidermis by identifying a heartbeat, body heat, skin recognition. Furthermore, the biometric sensor 90 detects the presence of skin and/or eyes through thermal or skin recognition, e.g., using backscatter or blue LED technology. Various types of biometric sensors are within the scope of this invention, including, but not limited to heart rhythm, vein pattern, fingerprints, hand geometry, DNA, voice pattern, iris pattern, and face detection. Adaptive biometric sensing is also within the scope of this invention. For example, the biometric sensor 10 and processor 68 are programmed to distinguish one user, or more importantly one individual exposed to far-UVC light from another using heartbeat, vein recognition or the like. As will be explained further hereinbelow, the device 10 will automatically terminate illumination when an individual has been exposed to the far-UVC light to a predetermined threshold or limit. The biometric sensor 90 distinguishes between multiple users deactivating the device 10 when a given use has met threshold limits but allowing activation for another use who has not yet met threshold limits. The biometric sensor 90 identifies if multiple users are within the irradiation zone of the device 10 and signals the processor 68 to tabulate the amount of time any given user is within the irradiation zone thereby terminating illumination by the device 10. It should be understood that the processor 68 is programmed to correlate distance from the device 10 to epidermis with amount of far-UVC light energy is being transferred to the epidermis for the purpose of identifying whether predetermine threshold limits have been met. Therefore, epidermis in close proximity to the device 10 will be allowed less time of exposure than epidermis that is more distant from the device 10.

In some instances, it is also desirable to include an ability to detect pathogens that are either aerosol or disposed on a surface. As such, in another embodiment, the device 10 includes a pathogen sensor 91 for detecting and identifying any pathogens within the irradiation zone 64. Microbial sensors provided by Nuwave Sensors and equivalents may be use for rapid detection of airborne microbes. When detecting presence of surface pathogens, it is believed that long-range surface plasmon-enhanced fluorescence spectroscopy provides for rapid detection. Surface plasmon resonance sensors are an optical platform capable of highly sensitive and specific measuring of biomolecular interactions in real-time that provide rapid user feedback as to whether surface pathogens have been eradicated. If a pathogen is detected within the irradiation zone 64, the processor 68 maintains irradiation to ensure that the pathogen is eradicated. For example, the processor 68 maintains illumination by the lamp 26 until no further pathogens are detected, or until 2 Log, 3 Log or other eradication level has been achieved. Hospital settings may require 3 Log or even 4 Log reduction of pathogens while personal or other commercial uses may only require a 2 Log reduction. The processor 68 is programmable to adapt the device 10 for any of these desired eradication outcomes. In a still further embodiment, an audible indication or visible signal are generated to advise the operator no further pathogens have been detected so that the operator may at his or her discretion deactivate the device 10.

Figure 8:
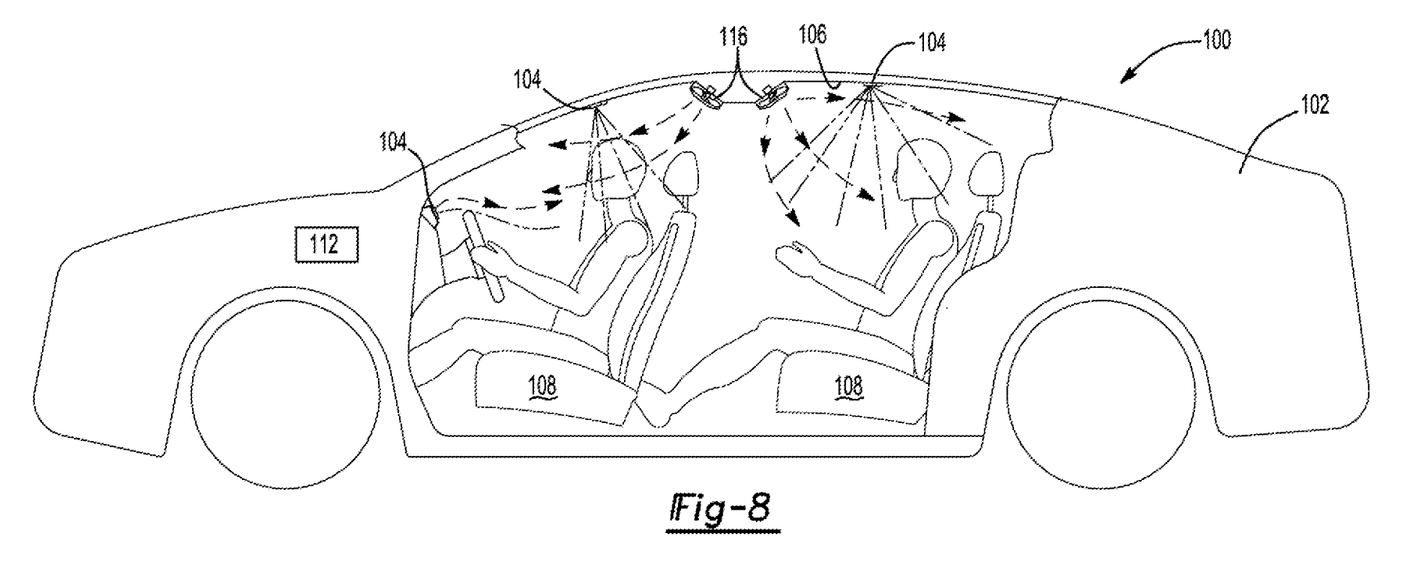
FIG. 8 shows a second embodiment of a system of the present invention implemented in a vehicle.
Figure 9:
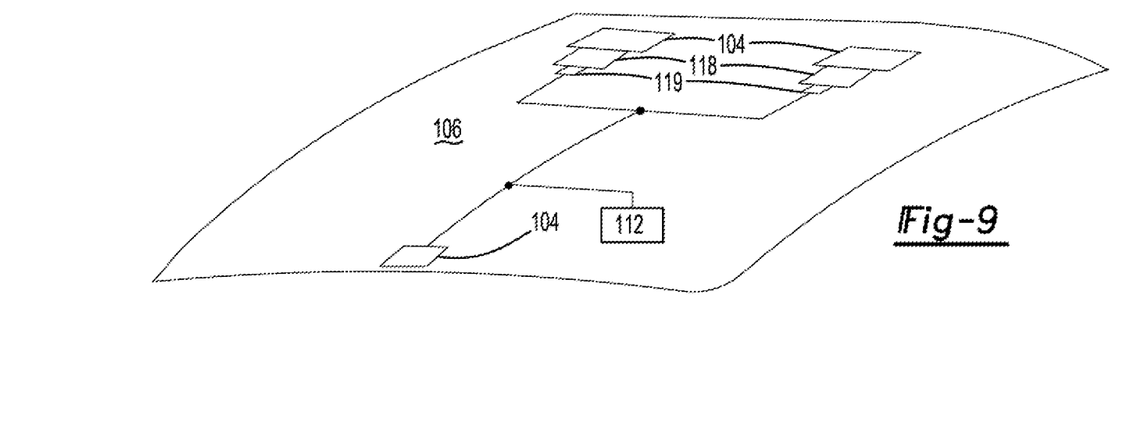
FIG. 9 shows a perspective view of a headliner system from the vehicle depicted in FIG. 8.
Figure 10:
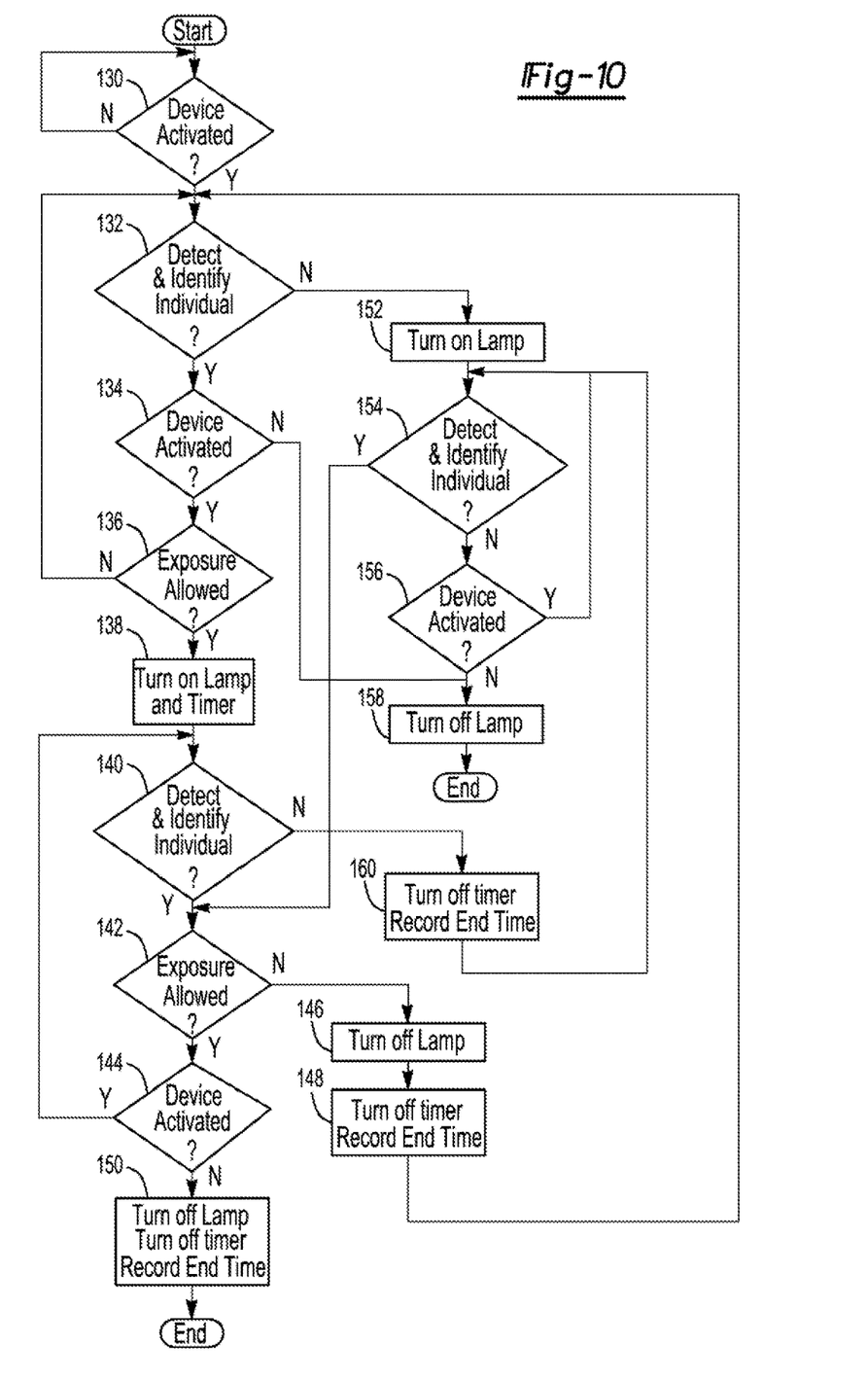
FIGS. 10 shows a flow diagram illustrating the operation of the device of FIG. 1A.

Further uses of pathogen eradication are desirable in confined spaces, such as, for example, passenger vehicles, airplanes, and the like. FIGS. 8-10 depict a further embodiment of a system 100 for safely eradicating pathogens that is implemented in a vehicle 102. It should be understood that while a passenger vehicle is shown, the invention of the present application may be implement in any vehicle in which passengers ride, including, but not limited to, busses, cabs, rideshare vehicles, fully or autonomous vehicles and even airplanes. The vehicle 102 includes far-UVC lamps 104 integrated into the headliner 106 of the vehicle 102 that operate in a similar manner as does the handheld assemblies 10 set forth above and may also be removable from the headliner 106 for handheld use. It should be understood that while headliners are referred to throughout the specification the lamp 104 may be integrated with any interior trim component, including, but not limited to seats, pillar covers, speaker grilles, door panels, steering wheels and columns, instrument panels and the like. The lamps 104 not only eradicate pathogens on the vehicle seats 108, and other interior surfaces, but the lamps 104 also eradicate pathogens on any passengers 110 seated within the vehicle 102 as well as the surrounding air within the vehicle 102, as will be discussed further below. The lamps 104 are controlled by a processor 112 via electrical cables 114, both of which are integrated into the headliner 106. Alternatively, the processor 112 is placed anywhere within the vehicle 102, integrated with the main vehicle processor, and may even communicate with the lamps 104 wirelessly. The processor 112 is programmed in the same manner as is the processor 68 disposed in the handheld device 10. In this embodiment, the system 110 also includes fans or air circulation devices 116 integrated into the headliner 106 proximate to the lamps 104 or being integrated with the lamps 104. The fans 116 assist the vehicle HVAC system to circulate air that has been eradicated of pathogens by the lamps 104, and to direct air in the path of the lamp 104 irradiation zone as is identified in FIG. 8 with dashed lines to increase a probability that aerosol pathogens are directed into the irradiation zone of the lamp 104.

The vehicle-based system 100 further includes a biometric sensor 118 for detecting the presence of a passenger 110 within the vehicle 102. Similar to the biometric sensor 90 included with the handheld device 10, biometric sensor 118 may include a heartrate monitor or a fingerprint detector, or it may detect the presence of skin and/or eyes through thermal or skin recognition, e.g., using backscatter or blue LED technology as is described in the earlier embodiment hereinabove. The system also may include HVAC far-UVC lamps 120 within the HVAC system of the vehicle 102 to eradicate air that is circulated within the vehicle 102 from the ventilation system. As best represented in FIG. 8, a far-UVC lamp 120 is also locatable on or in an instrument panel 121 proximate an HVAC vent used to direct air throughout the vehicle 102 passenger compartment. In this manner, aerosolized pathogens are eradicated prior to air being circulated throughout the passenger compartment.

It is within the scope of this invention that the system 100 and the device 10 of the prior embodiment communicate via wireless transmission or over the internet so that multiple devices toll exposure of any user as a further safety precaution. Further, multiple devices, even integrate with a cellular phone app are provided wireless communication through Bluetooth or cellular services to toll exposure of a given user.

Still further, the vehicle-based system 100 optionally includes a pathogen sensor 119 for sensing aerosol or surface pathogens in the same manner as that described the earlier embodiment hereinabove. The system provides user or passenger input when pathogens are detected or even not detected. A passenger entering the vehicle is scanned by the pathogen sensor 119 for pathogens causing the system 100 to activate the lamps 120 when pathogens are detected. Alternatively, the doors of the vehicle 102 remain locked preventing a passenger from entering if pathogens are detected.

Scent may also be circulated within the vehicle 110 (instead of or in addition to the visible light) being indicative of pathogens or the lack thereof operating much like an air freshener. The scent may be customizable to the preferences of the user. The system 100 may indicate, when the scent fades, that the scent either needs to be replaced, and/or that the device needs to be recharged and/or the entire far-UVC system 100 needs to be replaced (e.g., when the lack of scent will indicate that the far-UVC lamp 120 is no longer eradicating pathogens in the air within the interior of the automobile), or just for stationary use when portably attached to, for example, a passenger vehicle air vent, the system 100 emits scents to denote when the lamps 120 are activated or when a lamp 120 needs to be replaced or recharged. For example, the system 100 may include an odor producing attachment that attaches within the interior of, or proximate to, a passenger vehicle ventilation system.

Figure 11:
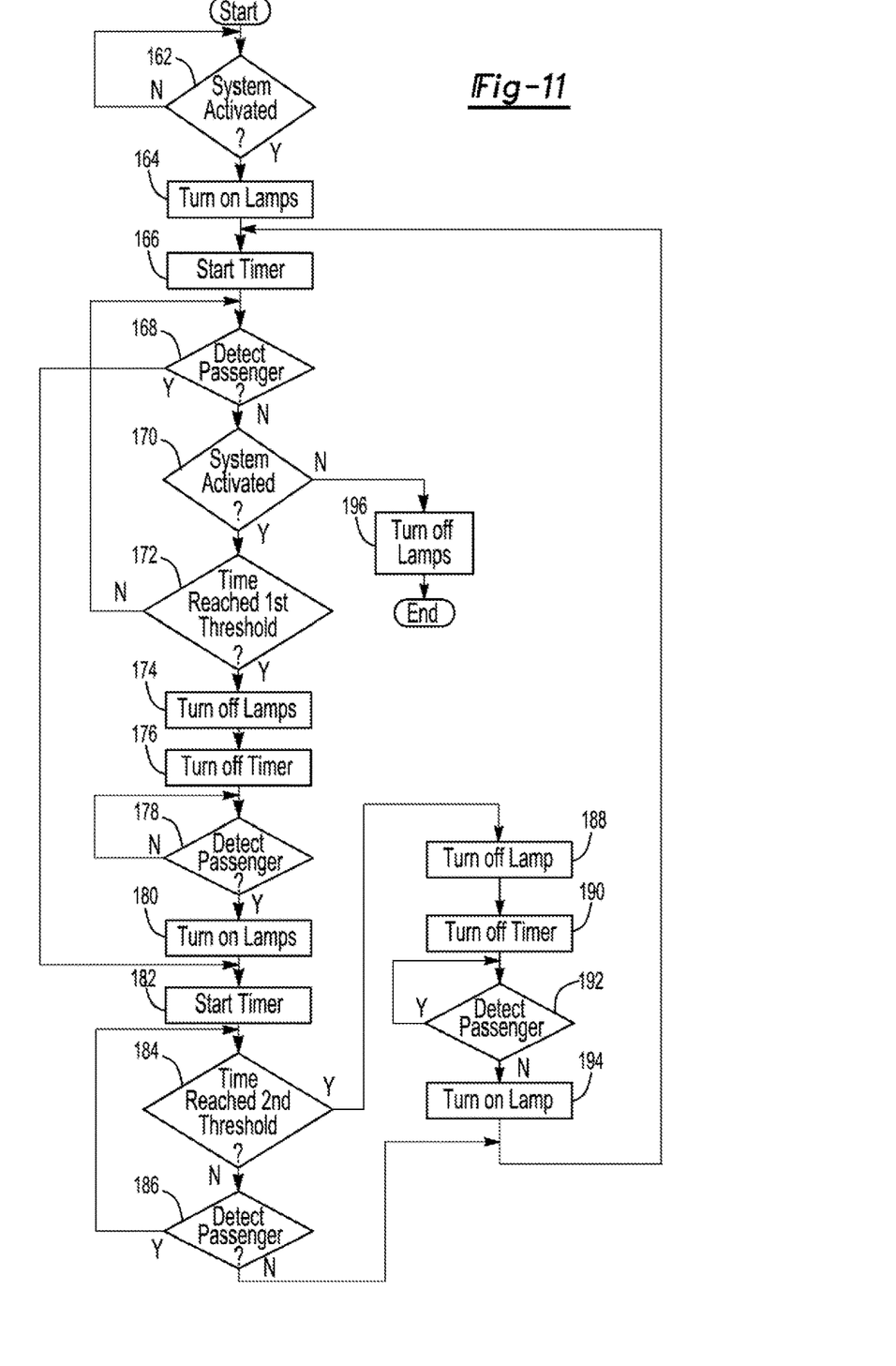
FIGS. 11 shows a flow diagram illustrating the operation of the pathogen eradication system in the vehicle shown in FIG. 8.

FIGS. 11 shows an exemplary method for operating the handheld light device 10. When the device 10 is activated (step 130), the sensor 90 determines whether an individual is within the irradiation zone 64 (step 132). If the sensor 90 determines that an individual has entered the irradiation zone 64, the sensor 90 identifies the specific individual (step 132) in order to track the amount of far-UVC light exposure the individual receives from the device 10. It is important to track the amount of far-UVC light exposure each individual receives because regulations governed by various non-government agencies limit the maximum duration of exposure to far-UVC light that a person may receive within a given exposure period. For example, under current regulations, an individual must limit the amount of exposure he or she has to far-LAC light to predetermined threshold limits. To ensure that the specific individual within the irradiation zone 64 does not exceed the recommended limits, the processor 68 tracks the amount of time that the specific individual is exposed to the far-UVC light by implementing a timer or counter. If the device 10 is still activated (step 134), the processor 68 determines whether the specific individual may be exposed with far-UVC light from the device 10 (step 136). In other words, the processor 68 determines if the specific individual has already reached his or her maximum duration under the regulations. If the processor 68 determines that the specific individual has met threshold limits for exposure to far-UVC light from the device 10, the processor 68 remains in the loop (steps 132, 134 and 136) until either the individual leaves the irradiation zone 64 at step 132, or the device is inactivated at step 134. Because the regulations are periodically updated, the present invention updates the maximum duration that an individual may be exposed to far-UVC light from the device 10 via a website, or via mobile pairing with the device 10 to update the software and; or code.

If at step 136, the processor 68 determines that the specific individual is allowed to be exposed to far-UVC light from the device 10, the processor 68 turns on the lamp 26 and starts the timer for the specific individual to keep track of the amount of time the specific individual is exposed to far-UVC light from the device 10 (step 138). The sensor 90 continues to monitor whether the specific individual remains within the irradiation zone 64 (step 140), and the processor 68 monitors the time the individual remains within the irradiation zone 64 to ensure that he or she does not exceed the maximum duration (step 142) while the device 10 is still activated (step 144). If at step 142, the processor 68 determines that the specific individual has reached his or her maximum duration and is no longer allowed to be exposed to far-UVC light from the device 10, the processor 68 turns off the lamp 26 (step 146), turns off the specific individual's timer and records the time as the individual's last exposure to far-UVC light (step 148). The system then returns to the loop 132, 134, 136, and waits for the individual to leave the irradiation zone 64.

If at step 144, the processor 68 determines that the device 10 is no longer active, the processor 68 turns off the lamp 26, turns off the individual's timer and records the end time as the individual's last exposure to far-UVC light (step 150). Threshold limits are based upon an eight or twenty-four-hour period after which the processor 68 resets the timer for each individual allowing additional exposure.

If at step 132, the sensor 90 does not detect an individual within the irradiation zone 64, the processor 68 turns on the lamp 26 (step 152). The sensor 90 continues to monitor whether an individual enters the irradiation zone 64 (step 154). If the sensor 90 determines that an individual has entered the irradiation zone 64, the processor 68 moves to step 142 to determine whether the specific individual may be exposed with far-UVC light from the device 10. If at step 154 the sensor does not detect an individual in the irradiation zone 64, the processor 68 remains in loop 154, 156 until it determines that the device 10 has been deactivated (step 156), at which point, the processor 68 turns off the lamp 26 (step 158). If at step 140 the specific individual leaves the irradiation zone 64, the processor 68 turns off the individual's timer and records the end time as the individual's last exposure to far-UVC light (step 160). The method then returns to step 154. As long as the device 10 is activated (step 156), the lamp 26 remains on until another individual is detected within the irradiation zone 64 (step 154). The use of biometric sensors for identifying individuals at which time the individuals are expose to the far-UVC light provides the failsafe ability for use of the device 10 while verifying threshold limits are not exceeded.

FIGS. 11A-B show an exemplary method for operating the eradication system 100 in passenger compartments and on passenger seats 108 within the vehicle 102 depicted in FIG. 8. When the system 100 is activated (step 162), the processor 112 turns the lamps 104 on (step 164) and starts a timer (step 166) to control the duration of the time that the lamps 104 are activated. The biometric sensor 118 determines whether a passenger 110 is in the vehicle seat 108 (step 168). If the biometric sensor 118 does not detect a passenger 110 in the vehicle seat 108, the processor verities the system is still activated (step 170). If the system is still activated, the processor 112 determines if the first threshold time period is reached (step 172). The first threshold time period is the duration of time that the lamps 104 are activated when no passengers 110 are detected within the vehicle seat 108. If the first threshold has been reached, the processor turns off the lamps 104 (step 174) and turns off the timer (step 176). At this point, the vehicle seat 108 and other surfaces have been eradicated of pathogens, and the system 100 waits for the entry of a passenger (step 178). After the entry of the passenger 110, the processor 112 turns on the lamps 104 (step 180) and starts the timer (step 182). The processor 112 determines if the tinier has reached the second threshold, which is the maximum amount of time a passenger may be safely exposed to the far-UVC light or that enough time has lapsed that the pathogens have been eradicated.

If the second threshold is not reached, the system 110 continues to irradiate the passenger 110 in the vehicle seat 108 until either the second time threshold is reached (step 184) or the passenger 110 leaves the vehicle (step 186). If the processor determines that the second time threshold has been reached, the processor 112 turns off the lamps 104 (step 188) and turns off the timer (step 190).

If the driver would like to eradicate any pathogens on himself or herself, the driver may activate the lamp 104 above the driver seat. The process would follow the steps 182-190 provided in FIG. 11B. Alternatively, the process may follow steps 140-150 provided for device 10.

The device 10 and/or the system 100 may also include a pathogen detecting sensor to target the time and intensity of the far-UVC light applied to target the specific pathogen.

The invention has been described is in an illustrative manner; many modifications and variations of the present invention are possible, including removal of toxins from fluids, in light of the above teachings. It is therefore to be understood that within the specification, the reference numerals are merely for convenience, and are not to be in any way limiting, and that the invention may be practiced otherwise than is specifically described. Therefore, the invention can be practiced otherwise than is specifically described within the scope of the stated claims following this first disclosed embodiment.

What is claimed is:

1. A system for eradicating pathogens inside a passenger compartment of a vehicle, comprising:
   a lamp transmitting far ultraviolet C (far-UVC) light thereby generating an irradiation zone within the passenger compartment of the vehicle;
   an interior trim component having said lamp integrated therewith;
   an air circulation system for circulating air through said irradiation zone of said. lamp thereby eradicating aerosol pathogens disposed within the passenger compartment; and
   said lamp directing said irradiation zone toward passengers and surfaces of the interior of the vehicle thereby eradicating pathogens disposed on at least one of the passengers and surfaces of the interior of the vehicle.

2. The system set forth in claim 1, wherein said interior trim component comprises one of a headliner, HVAC vent, instrument panel, door panel, pilar cover, seat, and steering wheel and column.

3. The system set forth in claim 1 wherein said air circulation system comprises one of a fan or HVAC system of the vehicle.

4. The system set forth in claim 1, further including a biometric sensor system for detecting epidermis of a passenger exposed within said irradiation zone.

5. The system set firth in claim 4, wherein said biometric sensor system is electronically connected to a processor being programmed for identifying individuals having epidermis exposed with said irradiation zone.

6. The system set forth in claim 5, wherein said processor terminates transmission of far-UVC light by said lamp when epidermis of an individual is exposed to said irradiation zone beyond a predetermined threshold.

7. The system set forth in claim 1, further including a pathogen sensor for sensing existence of pathogens disposed within the passenger compartment of the vehicle.

8. The system set forth in claim 7, wherein said pathogen sensor comprises one of one of a microbial sensor for sensing aerosol pathogens and a surface plasmon resonance sensor for sensing surface pathogens.

9. The system set forth in claim 8, wherein said pathogen sensor is electronically connected to said processor for signaling said processor initiate irradiation by said lamp.

10. The system set forth in claim 9, wherein said processor is programmed to prevent access to the passenger compartment of said vehicle when said pathogen sensor sensed presence of a pathogen inside the passenger compartment of the vehicle.

11. The system set forth in claim 1, wherein said lamp is disposed in a handheld device being removable from the interior trim component.

* * * * *